(12) United States Patent
Witte (10) Patent No.: US 11,597,063 B2
(45) Date of Patent: Mar. 7, 2023

(54) TORQUE LIMITER

(71) Applicant: Peter Witte, Kiel (DE)

(72) Inventor: Peter Witte, Kiel (DE)

( * ) Notice: Subject to any disclaimer, the term of this patent is extended or adjusted under 35 U.S.C. 154(b) by 205 days.

(21) Appl. No.: 17/149,195

(22) Filed: Jan. 14, 2021

(65) Prior Publication Data

US 2021/0146514 A1    May 20, 2021

Related U.S. Application Data (63) Continuation-in-part of application No. 16/278,683, filed on Feb. 18, 2019, now abandoned, which is a continuation-in-part of application No. PCT/DE2017/100669, filed on Aug. 8, 2017.

(30) Foreign Application Priority Data

Aug. 19, 2016 (DE) ............... 20 2016 104 553.3

(51) Int. Cl.
| | |
|---|---|
| *B25B 23/142* | (2006.01) |
| *A61B 17/88* | (2006.01) |
| *F16D 43/208* | (2006.01) |
| *A61B 90/00* | (2016.01) |

(52) U.S. Cl.
CPC ...... *B25B 23/1427* (2013.01); *A61B 17/8875* (2013.01); *A61B 90/03* (2016.02); *F16D 43/208* (2013.01); *A61B 2090/031* (2016.02)

(58) Field of Classification Search
CPC . B25B 23/1427; A61B 17/8875; A61B 90/03; A61B 2090/031; F16D 43/208

USPC .......................................................... 464/37
See application file for complete search history.

(56) References Cited

U.S. PATENT DOCUMENTS

| 4,744,447 A | 5/1988 | Kato et al. |
|---|---|---|
| 2011/0042176 A1 | 2/2011 | Witte |

FOREIGN PATENT DOCUMENTS

| DE | 202006004027 U1 | 6/2006 |
|---|---|---|
| FR | 1220285 A | 5/1960 |
| JP | H06341454 A | 12/1994 |
| JP | H0735170 A | 2/1995 |
| SU | 609002 A1 | 5/1978 |

*Primary Examiner* — Greg Binda
(74) *Attorney, Agent, or Firm* — Rankin, Hill & Clark LLP (57) ABSTRACT

A torque limiter for a surgical screwdriver that includes an outer sleeve (1); a snap sleeve (3), which is arranged in and rotates with the outer sleeve; a rolling element cage (6), which is arranged in the snap sleeve; an inner sleeve (10), which is arranged in the rolling element cage; and a force-transmitting shaft (11), which is received in and rotates with the inner sleeve. The inner wall of the outer sleeve is provided with recesses (8) that extend parallel to a rotational axis of the force-transmitting shaft. The rolling element cage is provided with a plurality of rolling element receiving areas (5), each of which holds a rolling element (4), and with a number of noses (7), which engage into the recesses. The inner sleeve is provided with a plurality of notches (9), which extend in a V-shape parallel to the axis and which receive the rolling elements.

5 Claims, 11 Drawing Sheets

Fig. 2

Fig. 4
III-III

TORQUE LIMITER

CROSS-REFERENCE TO RELATED APPLICATIONS

This application is a continuation-in-part of U.S. application Ser. No. 16/278,683, filed Feb. 18, 2019, now abandoned, which is a continuation-in-part of International App. No. PCT/DE2017/100669, filed Aug. 8, 2017, and claims priority to German Patent App. No. 20 2016 104 553.3, filed Aug. 19, 2016.

BACKGROUND OF INVENTION

Field of Invention

The present invention relates to a torque limiter, in particular a torque limiter for limiting the torque of a surgical screwdriver.

Brief Description of Related Art

A torque limiter for a surgical screwdriver is disclosed in DE 20 2006 004 027. In this torque limiter, a problem arises in that the elasticity of the elastic element configured as an elastomer O-ring significantly varies and changes over time, in particular as a result of thermal stress.

An object of the invention is to provide a torque limiter in which the maximum torque which is able to be transmitted may be determined with a greater degree of accuracy and does not change significantly, even as a result of thermal stress on the torque limiter—namely during the sterilization thereof.

According to the invention, this object is achieved by a torque limiter as disclosed and claimed herein.

BRIEF SUMMARY OF THE INVENTION

According to the invention, a torque limiter is provided, in particular for a surgical screwdriver. The torque limiter comprises an outer sleeve, a snap sleeve which is rotationally fixed in the outer sleeve and a rolling element cage, which is arranged in the snap sleeve. The torque limiter further comprises an inner sleeve, which is arranged in the rolling element cage, and a force-transmitting shaft, which is received by the inner sleeve in a rotationally fixed manner. The inner wall of the outer sleeve is provided with recesses extending parallel to the axis. The rolling element cage is provided with a plurality of rolling element receiving areas, each of which holds a rolling element. The rolling element cage is also provided with a number of noses. The noses engage into the recesses. The width of the noses is less than the open width of the recesses. The number of noses corresponds to the number of recesses. The inner sleeve is provided with a plurality of V-shaped notches, which extend parallel to the axis and which are used to receive the rolling elements. When a torque is applied to the outer sleeve in the screwing direction, it presses one side of the noses against one of the walls of the recesses into a position in which the rolling elements (that are slightly offset relative to the noses) are flush with the recesses. This allows the rolling elements to exit the V-shaped notches of the inner sleeve into the recesses of the outer sleeve (spreading the snap sleeve) when a maximally permissible torque is reached, thereby uncoupling the inner sleeve. When a torque is applied to the outer sleeve in the unscrewing direction, it presses the other side of the noses against the other wall of the recesses into a position in which the rolling elements are flush with the webs remaining between the recesses. This prevents the rolling elements from exiting the V-shaped notches of the inner sleeve, thereby coupling the inner sleeve.

By means of this coupling, a positive connection is made between the outer sleeve and the inner sleeve. By means of this mechanism, an unlimited transmission of force is ensured in the unscrewing direction. In this position, the snap sleeve is uncoupled from any actions of force. As a result, a long functional life of the torque limiter as a whole, a consistent accuracy and thus the reproducibility of the actuating torques are ensured.

Preferably, the rotational fixing between the outer sleeve and the snap sleeve is effected by the provision of a drive element on the inner wall of the outer sleeve, said drive element protruding radially inwardly and engaging in the slot in the snap sleeve.

Further preferably, the rolling elements are configured as pins and the rolling element receiving areas are configured as slots.

According to an even further preferred embodiment, specifically the shaft is provided at its tip with a cone supported in a bearing cap.

It is advantageous if the snap sleeve is produced from a polyetheretherketone (PEEK).

The foregoing and other features of the invention are hereinafter more fully described below, the following description setting forth in detail certain illustrative embodiments of the invention, these being indicative, however, of but a few of the various ways in which the principles of the present invention may be employed.

BRIEF DESCRIPTION OF THE DRAWINGS

The present invention is described hereinafter with reference to the accompanying drawings, in which.

DETAILED DESCRIPTION OF THE INVENTION

Figure 1:
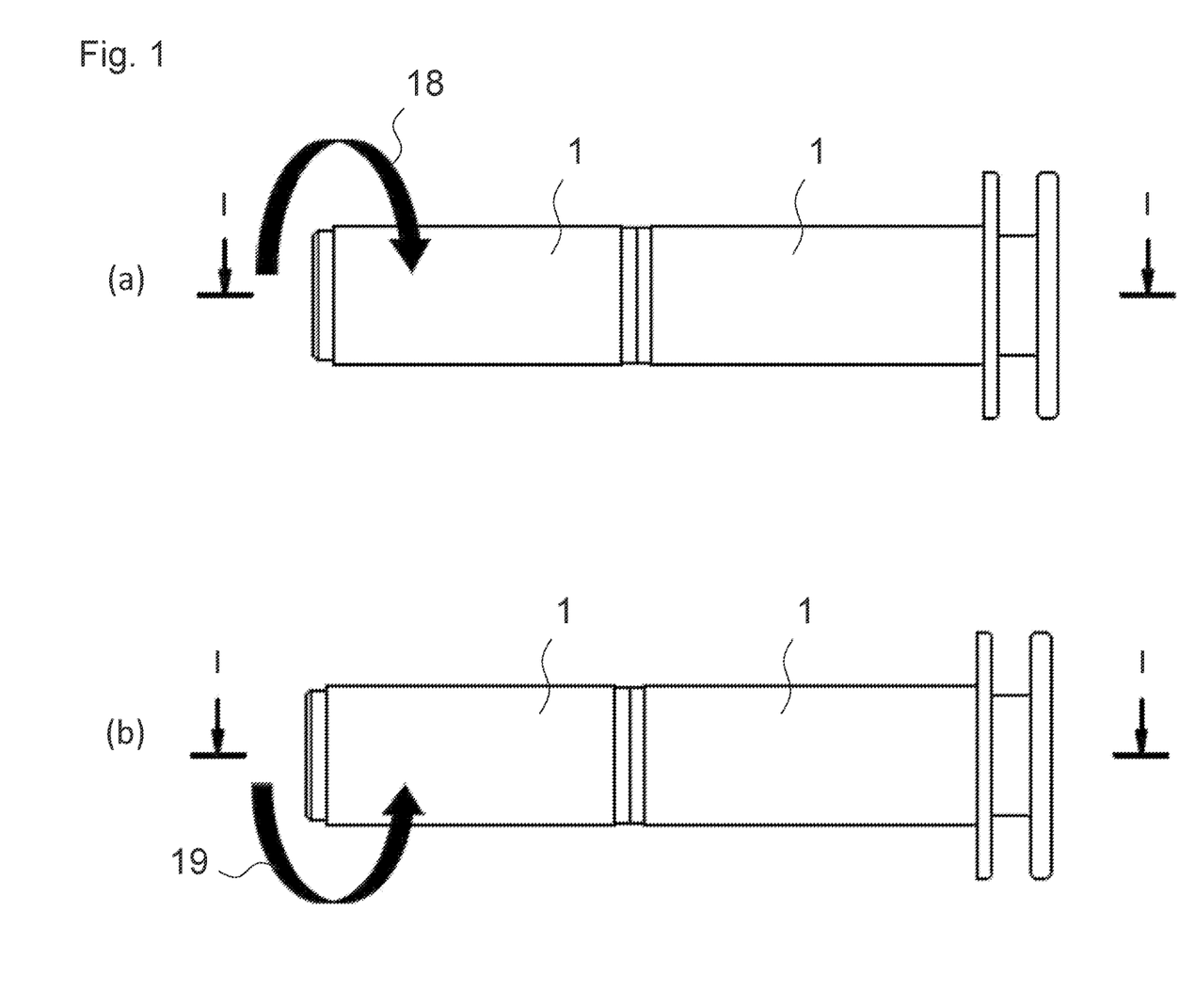
FIG. 1 shows an outer view of an exemplary embodiment of a torque limiter according to the invention ((a) shows the starting direction and (b) shows the release direction)

The figures show a torque limiter, in particular for a surgical screwdriver. The figures marked with (a) denote the torque limiter in the position when torque is applied in the starting direction 18, also known as the screwing direction 18. The figures marked with (b) denote the torque limiter in the position when torque is applied in the release direction 19, also known as the unscrewing direction 19. FIGS. 1(*a*) through 6(*b*) were created with a program for computer-aided design (CAD). The torque limiter comprises an outer sleeve 1, a snap sleeve 3 which is rotationally fixed in the outer sleeve; a rolling element cage 6 which is arranged in the snap sleeve, an inner sleeve 10 which is arranged in the rolling element cage and a force-transmitting shaft 11 which is received by the inner sleeve in a rotationally fixed/manner. This arrangement is best understood in connection with FIGS. 3(*a*) to 6(*b*).

Figure 4:
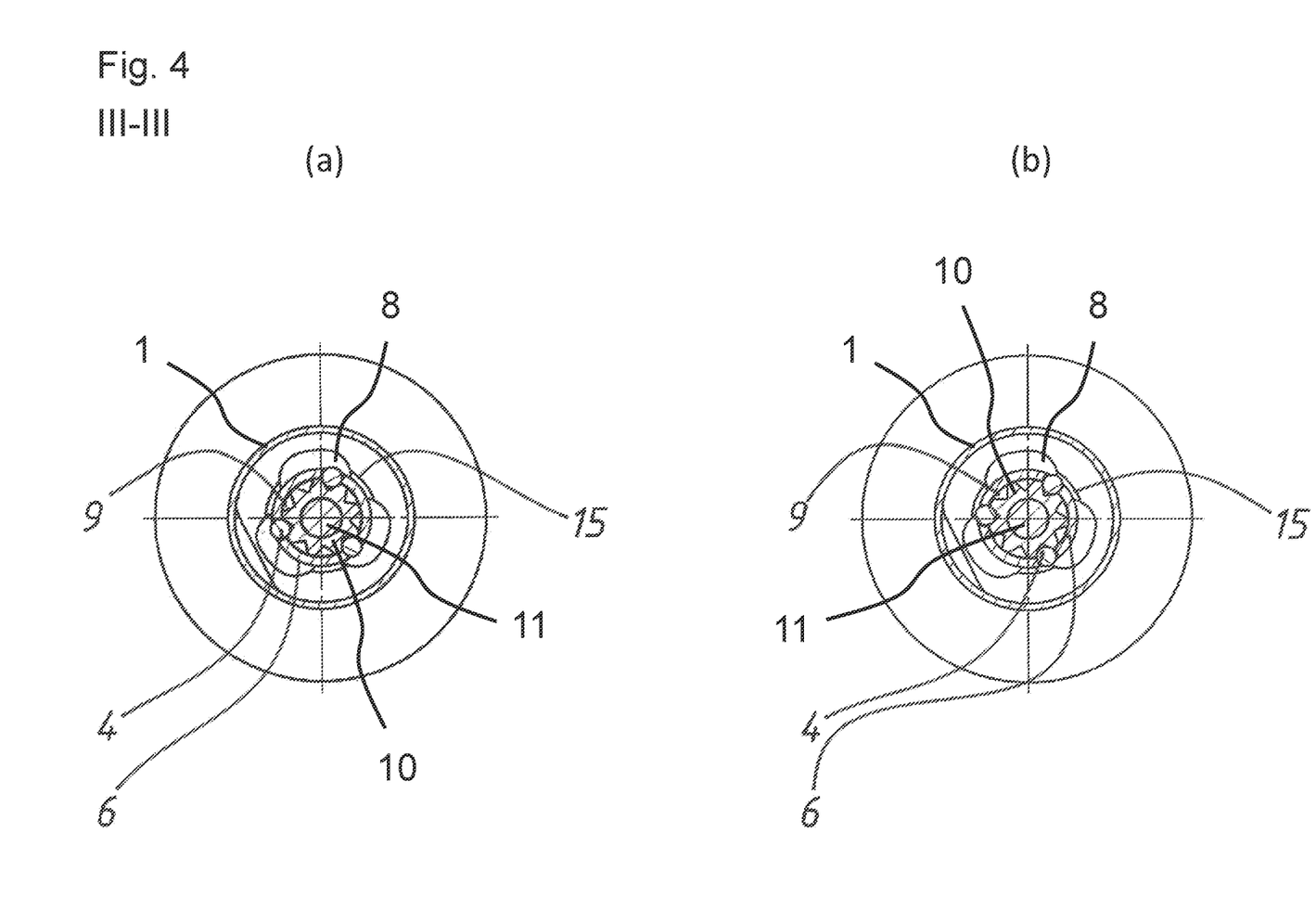
FIG. 4 shows a sectional view along the line III-III of FIG. 2 ((a) shows the starting direction and (b) shows the release direction)

The inner wall of the outer sleeve 1 is provided with recesses 8 extending parallel to the axis of rotation of the force-transmitting shaft, as shown in FIGS. 4(*a*), 4(*b*), 5(*a*), 5(*b*), 6*a* and 6*b*. The rolling element cage 6 is provided with a plurality of rolling element receiving areas 5, each of which holds a rolling element 4, and with a number of noses 7 which engage into the recesses 8 and the width of which is less than the open width of the recesses 8, said number corresponding to the number of recesses 8, and which are slightly offset relative to the rolling element receiving areas 5. The inner sleeve 10 has a plurality of notches 9 which extend in a V-shape parallel to the axis and which are used to receive the rolling elements 4.

Figure 2:
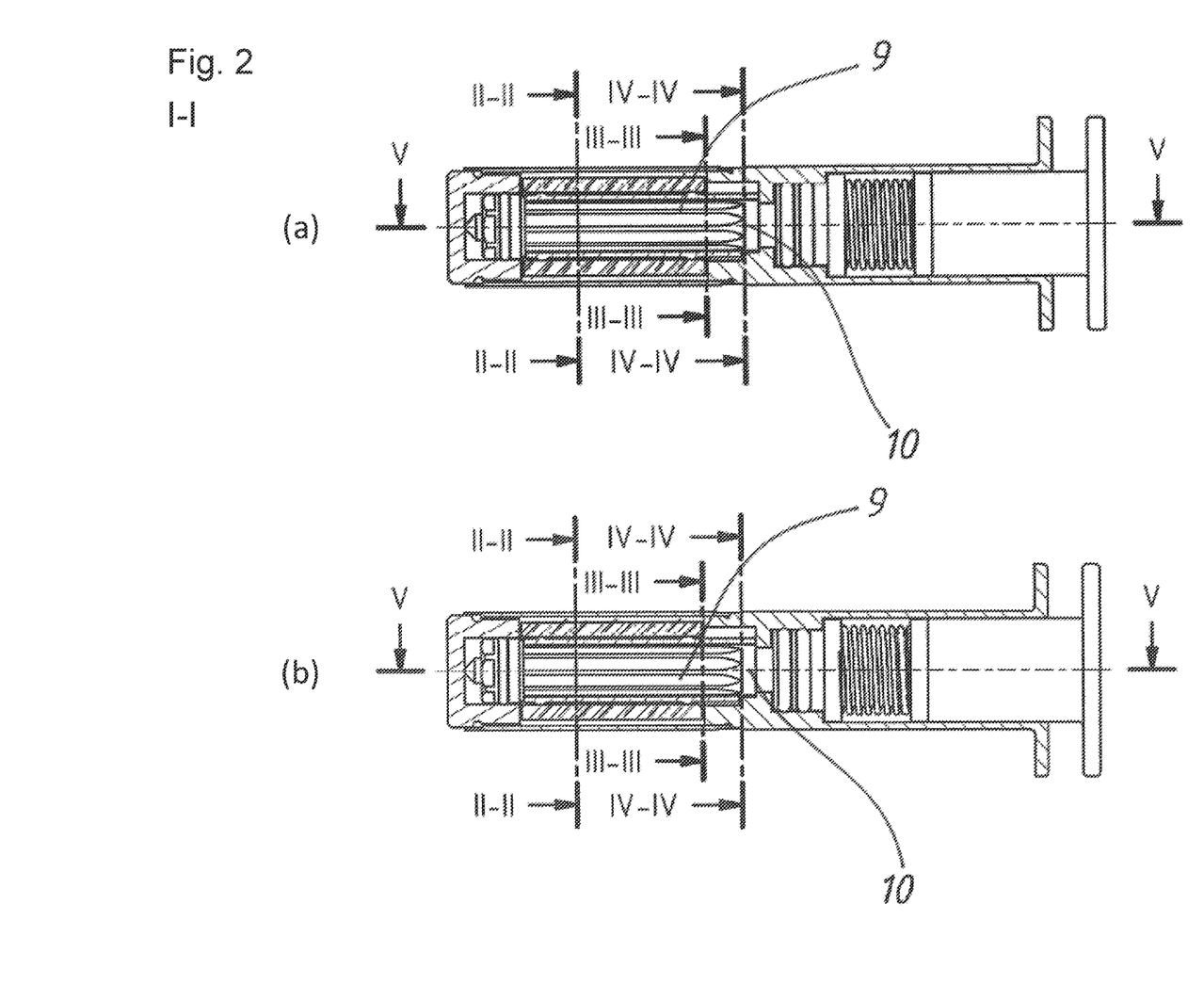
FIG. 2 shows a longitudinal sectional view of the torque limiter along the I-I direction of FIG. 1, showing the inner sleeve ((a) shows the starting direction and (b) shows the release direction)
Figure 3:
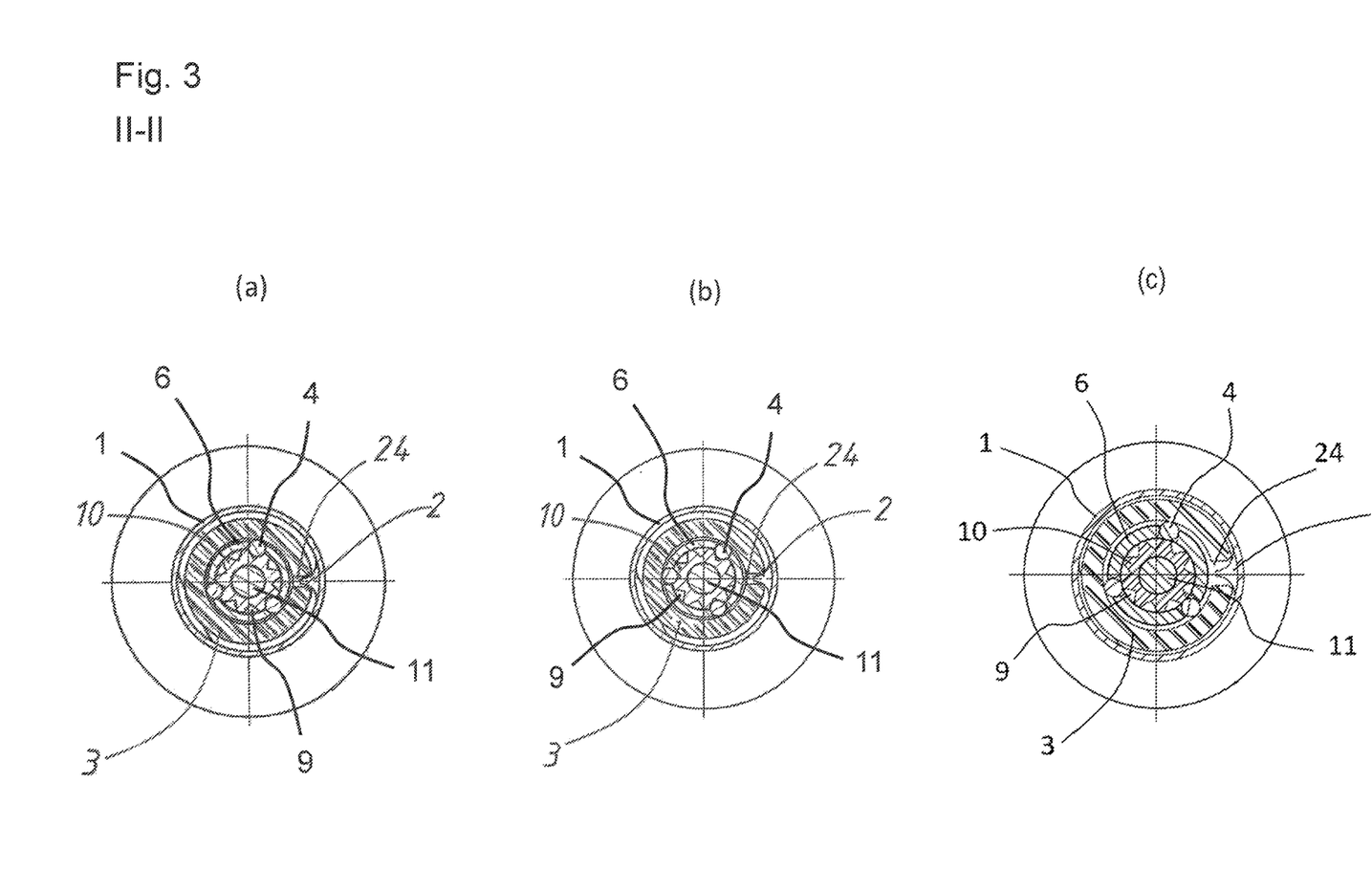
FIG. 3 shows a sectional view along the line II-II of FIG. 2 ((a) shows the starting direction, (b) shows the release direction, and (c) shows the expansion of the snap sleeve and position of the rolling elements relative to the inner sleeve during uncoupling of the inner sleeve from the outer sleeve)

A torque applied to the outer sleeve 1 in the screwing direction 18 presses one side 20 of the noses 7 of the rolling element cage 6 against one of the walls 22 of the recesses 8 into a position in which part of the rolling elements 4 (being the portion to the right of line III-III in FIG. 2) are flush with the recesses 8, thus allowing that part of the rolling elements 4 to exit the V-shaped notches 9 of the inner sleeve 10 into the recesses 8 of the outer sleeve 1 while the part of the rolling elements adjacent to the snap sleeve 3 (being the portion to the left of line III-III in FIG. 2) bear against and spread apart the snap sleeve 3 when a maximally permissible torque is reached, thereby uncoupling the inner sleeve 10 sleeve from the outer sleeve 1, as shown in FIG. 3(*c*). The snap sleeve 3 spreads into the gap between the snap sleeve 3 and the outer sleeve 1. This gap is for example shown in FIGS. 3(*a*) and 3(*b*). FIG. 4(*a*) shows a position in which the rolling elements 4 could exit the V-shaped notches 9 into the recesses 8, if the torque would be large enough to spread the snap sleeve 3.

A torque applied to the outer sleeve 1 in the unscrewing direction 19 presses the other side 21 of the noses 7 of the rolling element cage 6 against the other wall 23 of the recesses 8 into a position in which part of the rolling elements 4 (being the portion to the right of the line III-III in FIG. 2) are flush with the webs 15 remaining between the recesses 8. The webs 15 prevent the rolling elements 4 from exiting the V-shaped notches 9 of the inner sleeve 10 and thus also prevent the part of the rolling elements adjacent to the snap sleeve 3 (being the portion to the left of the line III-III in FIG. 2) from spreading apart the snap sleeve 3, thereby keeping the inner sleeve 10 coupled to the outer sleeve 1, as shown in FIG. 4(*b*). The form and position of the web 15 is also shown in FIGS. 6*a*, 6*b*, 7 and 9. When no torque is applied to the outer sleeve 1, the torque limiter is in an idle position. Depending on the direction in which torque was last applied to the outer sleeve 1, the idle position is identical to the position of the torque limiter when torque is applied in the screwing direction 18 or the unscrewing direction 19. Alternatively, the idle position can be a position in between those two positions. In such a position the noses 7 of the rolling element cage 6 do not press against any of the walls 22, 23 of the recesses.

In the exemplary embodiment shown, the rotational fixing between the outer sleeve 1 and the snap sleeve 3 is effected by the provision of a drive element 2 on the inner wall of the outer sleeve 1, said drive element protruding radially inwardly and engaging in the slot 24 in the snap sleeve 3, as shown in FIGS. 3(*a*) and 3(*b*).

In this case, the rolling elements 4 are configured as pins and the rolling element receiving areas 5 are configured as slots.

The shaft 11, which when used for a surgical instrument receives the instrument at its end 25 protruding the outer sleeve 1, is provided at its other end with a cone 12 mounted in a bearing cap 17. In this case, the tip of the cone 12 is oriented counter to the bearing cap and in practical use comes into contact therewith.

When using the torque limiter, a virtually friction-free mounting between the outer sleeve 1 and the inner sleeve 10 is achieved by means of the cone 12 mounted in the bearing cap. This structural feature minimizes the friction torques and enables a greater accuracy and thus reduced scattering of the adjusted torque.

Polyetheretherketone PEEK lends itself as the material for the snap sleeve 3, this plastics material being able to be easily sterilized whilst maintaining its elasticity.

A sealing nut 13 is positioned nearby the cone 12. A sealing disc 14 is also shown in FIG. 2. The sealing nut 13 and the sealing disc 14 are sealing the torque limiter against the surrounding, i.e. water vapor and seal or arrange the bearings of the shaft 11.

Connection systems known on the market, which are used to connect a medical instrument to a torque limiter, are frequently arranged as a separate coupling system outside of the torque limiter. This design entails many disadvantages. For example, contaminations can occur and bending torques are not compensated, which results in the occurrence of torque inaccuracies.

Figure 6A:
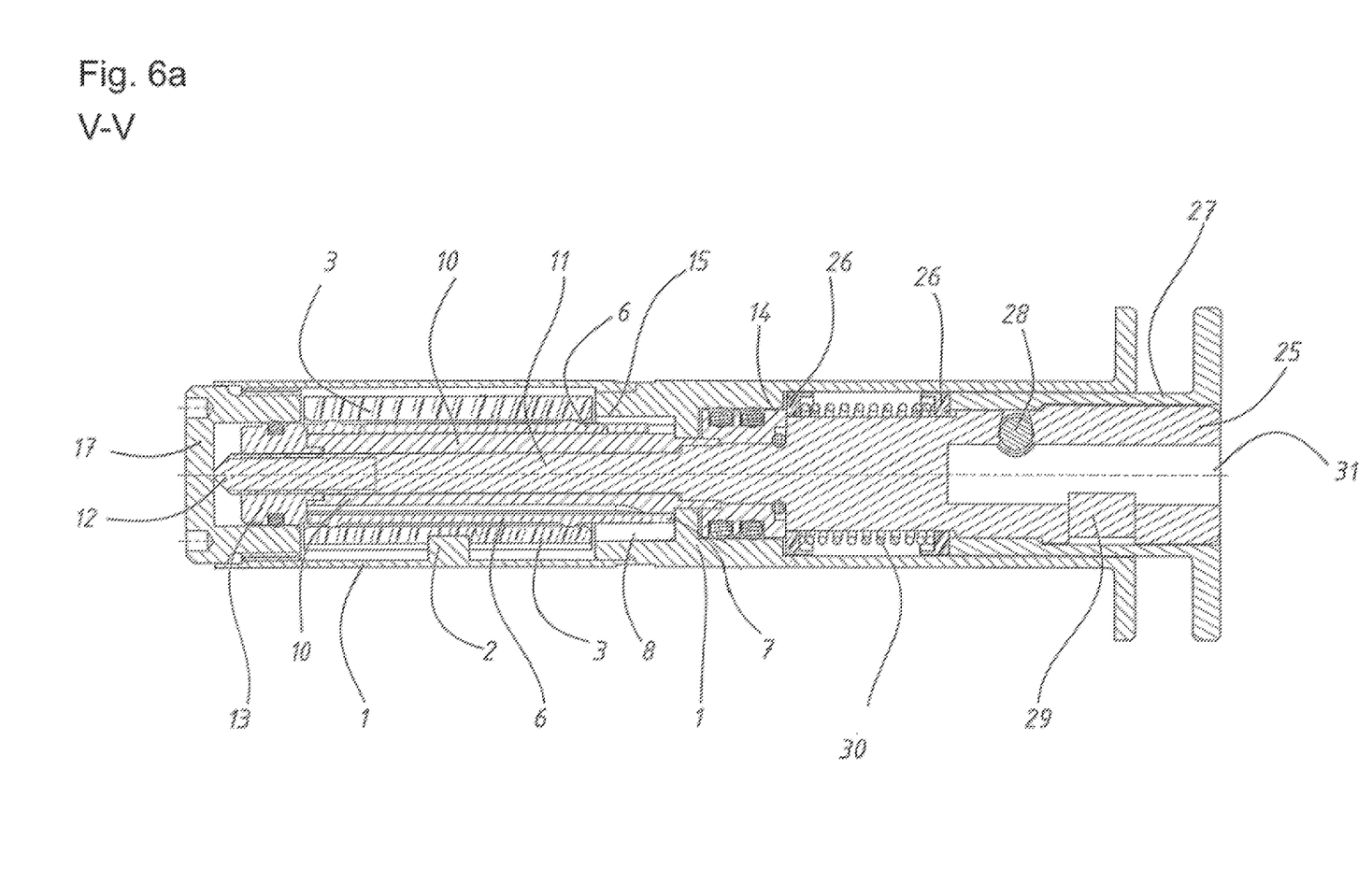
FIG. 6a shows a longitudinal sectional view of the torque limiter along the V-V direction of FIG. 2 in the starting direction.
Figure 6B:
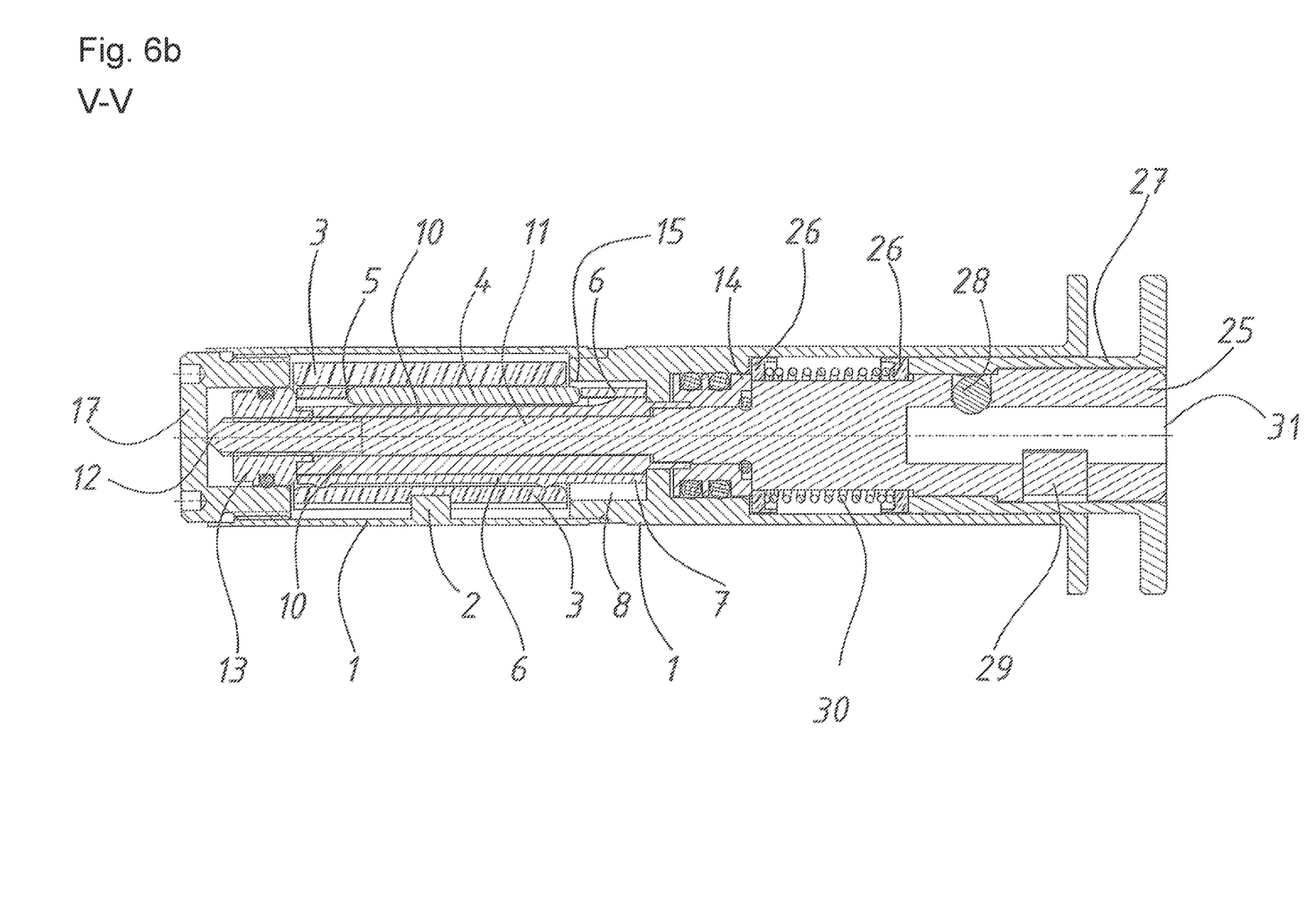
FIG. 6b shows a longitudinal sectional view of the torque limiter along the V-V direction of FIG. 2 in the release direction.
Figure 7:
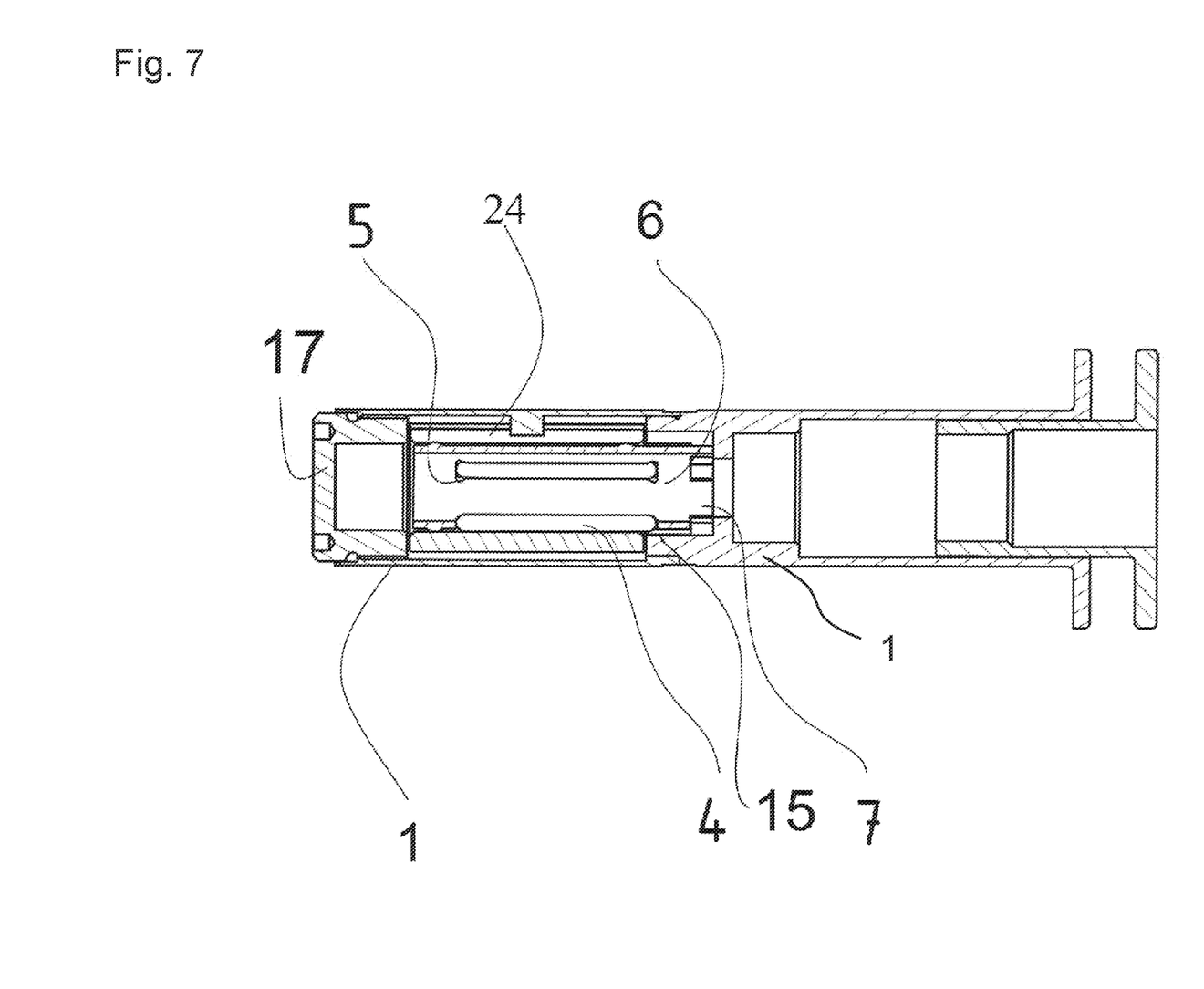
FIG. 7 shows a longitudinal sectional view of the torque limiter, showing the rolling element cage.

In order to avoid these disadvantages, the end 25 of the shaft 11 comprises a receptacle 31 designed to receive a medical instrument, as can be seen in FIGS. 6*a* and 6*b*. The receptacle 31 is integrated into a housing of the torque limiter. A plain bearing 26 and a slide sleeve 27 guide the receptacle 31 in the outer sleeve 1 in order to prevent tilting. Due to this constructive assembly the receptacle 31 is integrated angular-stable in the torque limiter and supported almost frictionless in the outer sleeve 1. Bending torques are compensated and a negative impact on the torque accuracy is prevented.

The medical instrument inserted in the receptacle 31 is secured by means of a locking element 28, preventing the medical instrument from falling out of the receptacle 31. The plain bearing 26 comprises two parts, wherein a spring element 30 is arranged in between these two parts. The spring element 30 allows the locking element 28 to be locked and unlocked. In addition, a safety element 29 of the receptacle 31 is provided as rotation lock of the inserted medical instrument.

In this way an accidental uncoupling of the medical instrument is prevented and the receptacle 31 can be adjusted for all connection geometries of medical instruments.

The described integration of the receptacle 31 in the housing of the torque limiter allows for a compact, ergonomic design and protects the connection system from contaminations.

Figure 5:
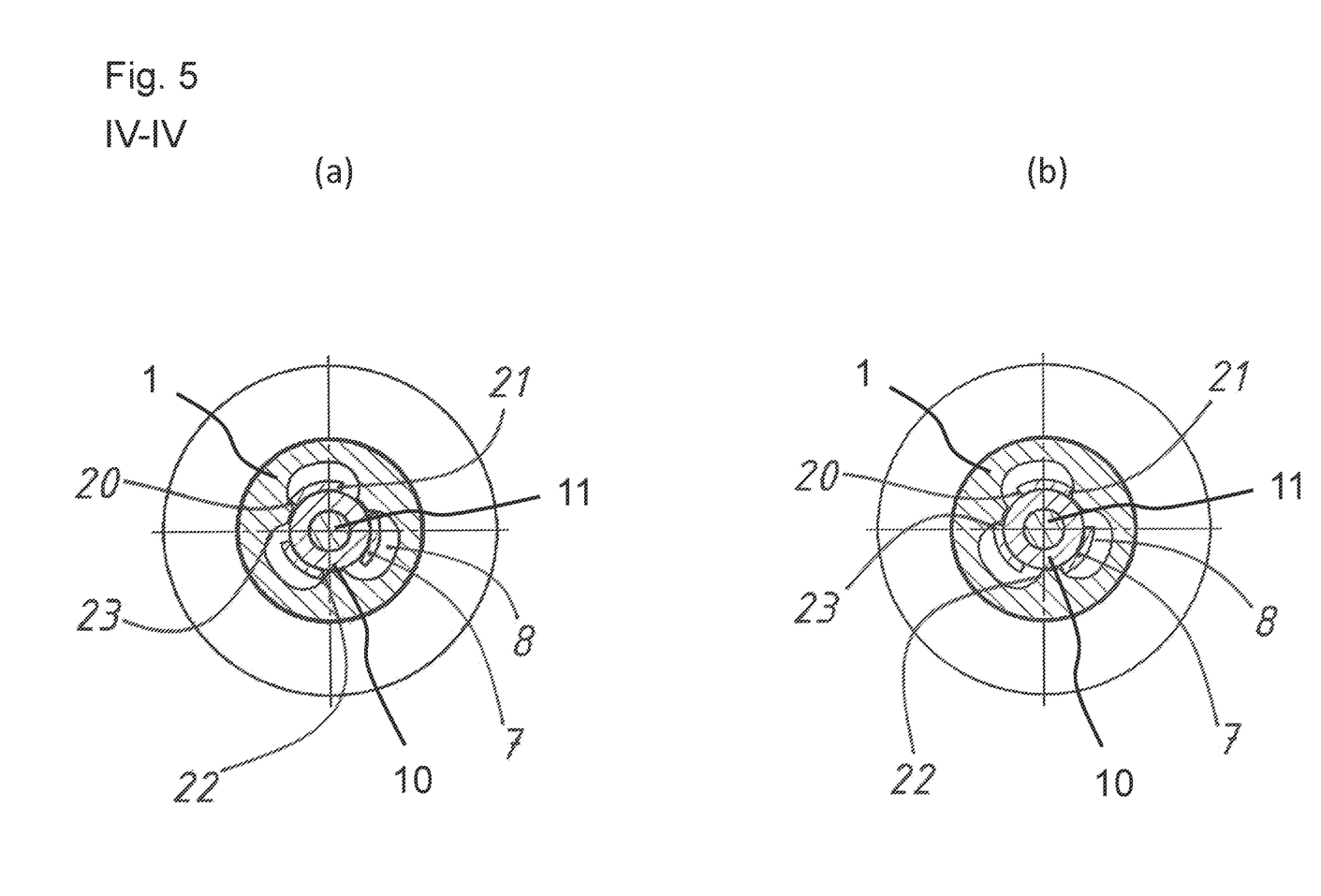
FIG. 5 shows a sectional view along the line IV-IV of FIG. 2 ((a) shows the starting direction and (b) shows the release direction)
Figure 8:
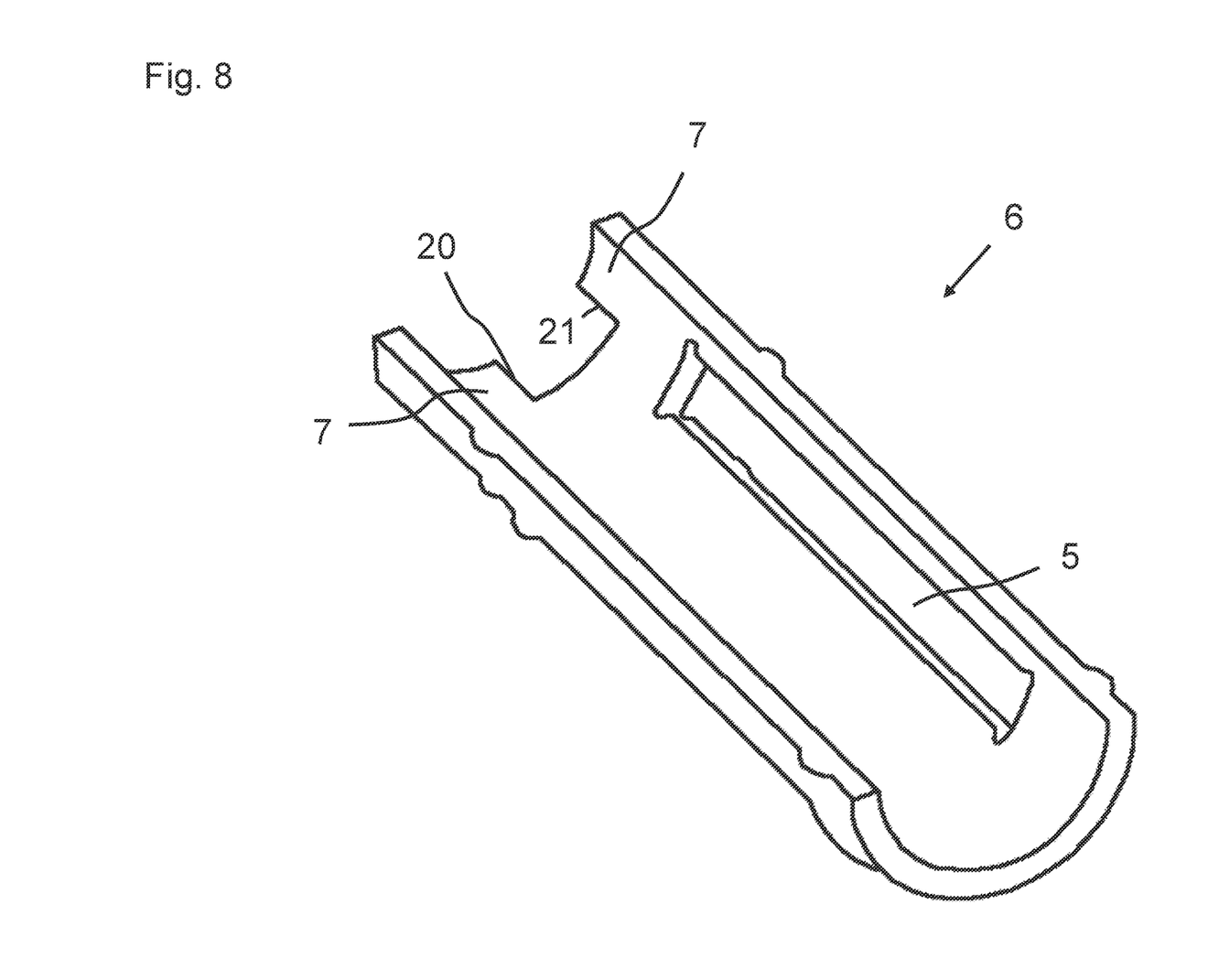
FIG. 8 shows a schematic perspective view of the rolling element cage cut along a horizontal plane.

FIG. 8 shows a schematic perspective view of the rolling element cage 6 cut along a horizontal plane. The noses 7 are part of the rolling element cage 6 and protrude from the rolling element cage 6. It can be seen that the noses 7 are slightly offset to the rolling element receiving areas 5 in a circumferential direction of the rolling element cage 6. Thus, when the noses 7 press against the other wall 23 of the recesses 8 (FIG. 5(b)), the rolling elements 4 are flush with the webs 15 (FIG. 4(b)), so that the rolling elements 4 cannot exit the V-shaped notches 9.

Figure 9:
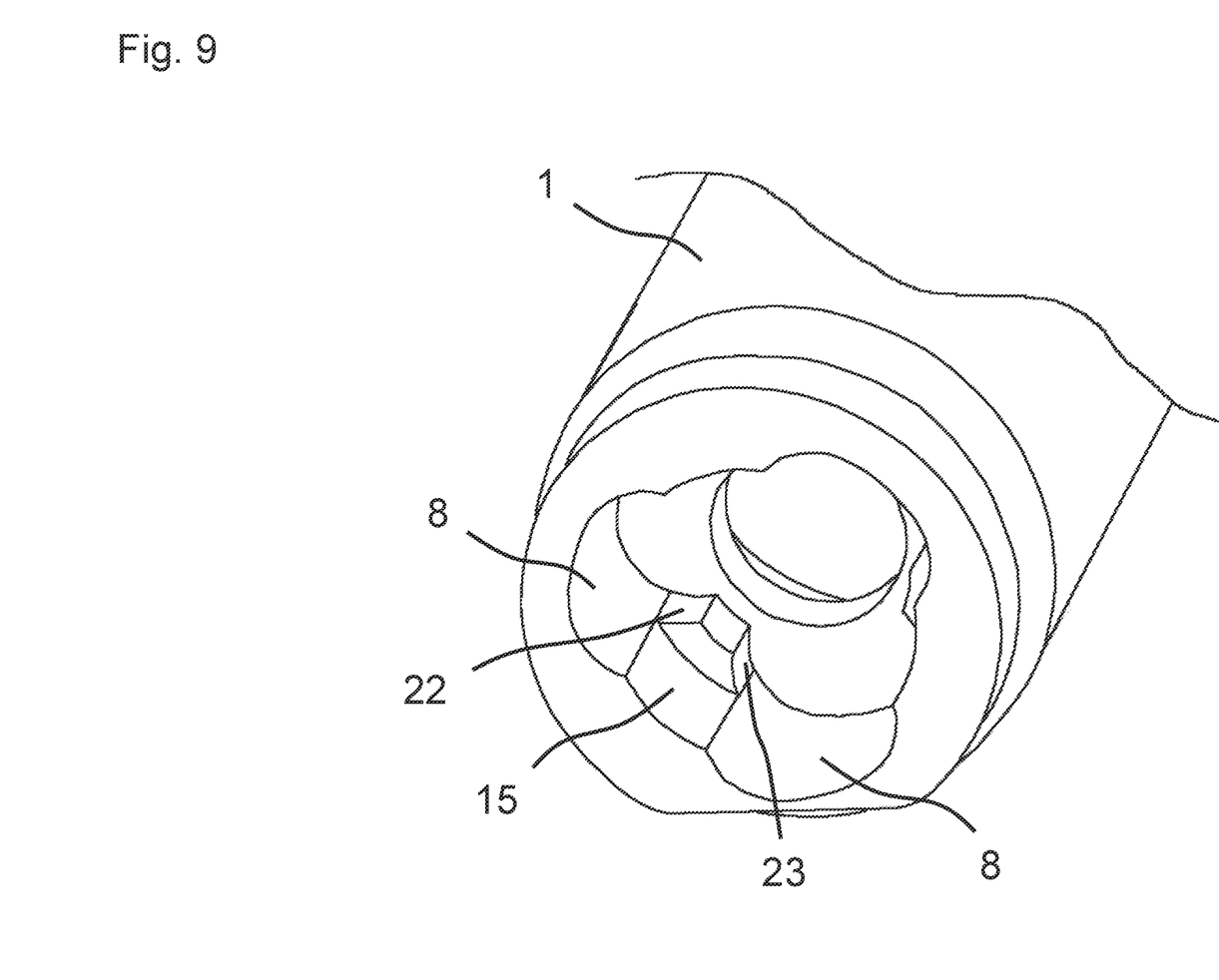
FIG. 9 shows a schematic perspective view of a rear section of the outer sleeve of the torque limiter cut along a cross sectional plane.

FIG. 9 shows a schematic perspective view of a rear section of the outer sleeve 1 of the torque limiter cut along a cross sectional plane. The cross sectional plane corresponds approximately to the III-III plane. FIG. 9 shows that the inside wall of the outer sleeve 1 in between the recesses is not uniform. A first part of this inner wall of the outer sleeve 1 forms the web 15, which prevents the rolling elements 4 from exiting the V-shaped notches 9 when a torque is applied in the unscrewing direction 19. A second part of this inner wall of the outer sleeve 1 protrudes further towards the center of the torque limiter and forms the walls 22, 23, which act as boundaries for the noses 7 of the rolling element cage 6.

Figure 10:
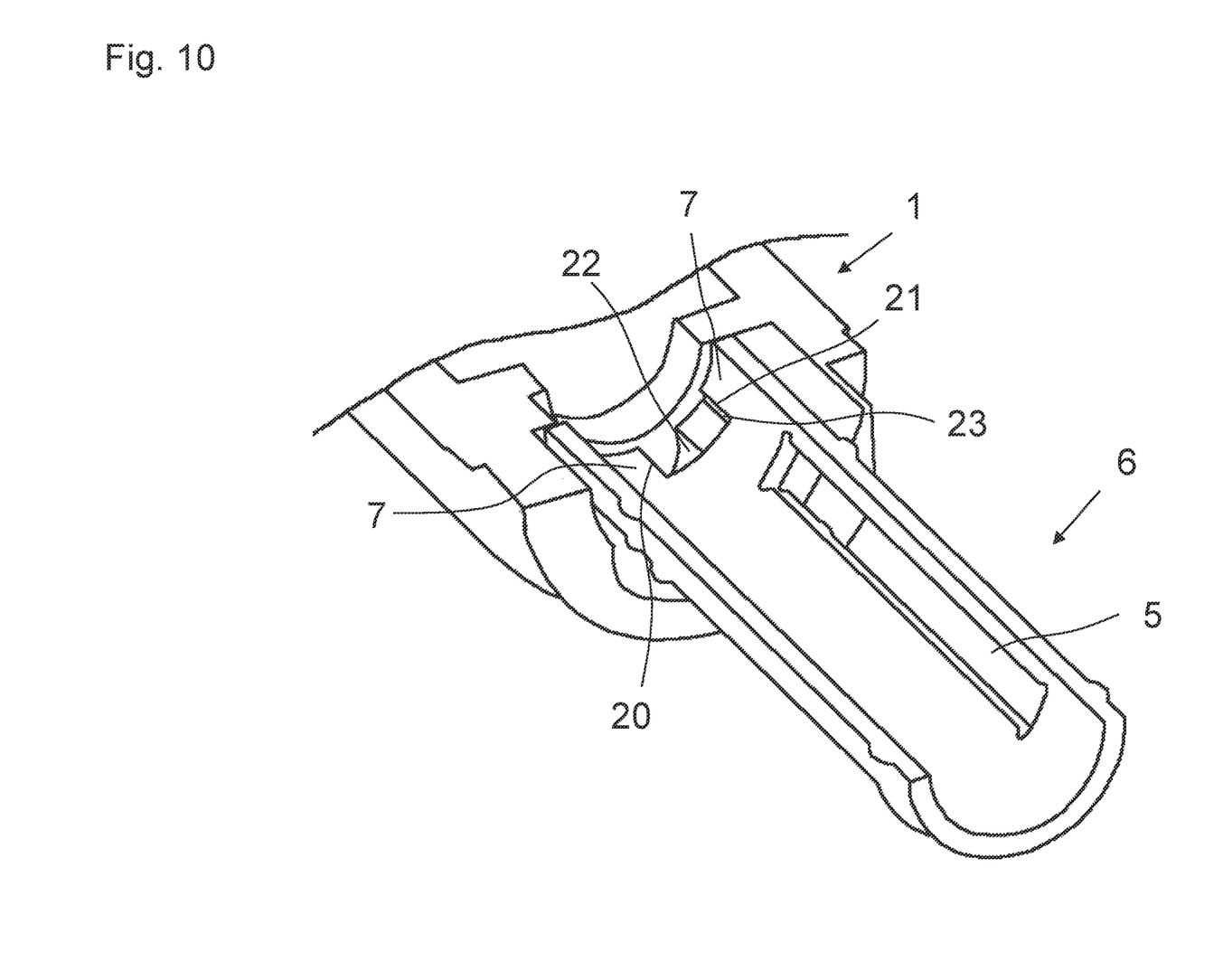
FIG. 10 shows a schematic perspective view of the rolling element cage of FIG. 8 inserted into a section of the outer sleeve.

FIG. 10 shows the rolling element cage 6 of FIG. 8 inserted into a section of the outer sleeve 1, which is cut along the same plane as the rolling element cage 6. FIG. 10 corresponds to a position of the torque limiter when a torque is applied in the unscrewing direction 19. Thus, there is a gap between the side 20 of the noses 7 and the wall 22 of the recesses 8. Meanwhile, the other side 21 of the noses 7 presses against the other wall 23 of the recesses 8.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A torque limiter for a surgical screwdriver comprising:
an outer sleeve;
a snap sleeve which is arranged in the outer sleeve and which is fixed to rotate with the outer sleeve;
a rolling element cage which is arranged in the snap sleeve;
an inner sleeve which is arranged in the rolling element cage; and
a force-transmitting shaft which is received within the inner sleeve and which is fixed to rotate with the inner sleeve;
wherein an inner wall of the outer sleeve is provided with a number of recesses that extend parallel to an axis of rotation of the force-transmitting shaft,
wherein the rolling element cage is provided with a plurality of rolling element receiving areas, each of which holds a rolling element such that the rolling element extends parallel to the axis of rotation of the force-transmitting shaft,
wherein a part of each rolling element is adjacent to the snap sleeve and another part of each rolling element extends beyond the snap sleeve,
wherein the rolling element cage is also provided with a number of noses, said number of noses corresponding to the number of recesses provided in the inner wall of the outer sleeve,
wherein the noses are configured to engage into the recesses provided in the inner wall of the outer sleeve,
wherein the noses have a width that is less than an open width of the recesses,
wherein the inner sleeve is provided with a plurality of V-shaped notches which extend parallel to the axis and which receive the rolling elements;
wherein, when a torque is applied to the outer sleeve in a screwing direction, sides of the noses of the rolling element cage are pressed against sides of walls of the recesses and the part of each rolling element that extends beyond the snap sleeve is flush with one of the number of recesses,
wherein when the torque applied to the outer sleeve in the screwing direction exceeds the ability of the snap sleeve to hold the rolling elements in the V-shaped notches of the inner sleeve, each part of the rolling element beyond the snap sleeve that is flush with one of the number of recesses exits the respective V-shaped notch of the inner sleeve into the one of the number of recesses of the outer sleeve while the part of each rolling element adjacent to the snap sleeve bears against and spreads apart the snap sleeve thereby uncoupling the inner sleeve from the outer sleeve,
when a torque is applied to the outer sleeve in an unscrewing direction, opposite sides of the noses of the rolling element cage are pressed against opposite sides of the walls of the recesses and the parts of each rolling element that extend beyond the snap sleeve are flush with webs remaining between the recesses,
wherein said webs prevent the rolling elements from exiting the V-shaped notches of the inner sleeve when the torque is applied to the outer sleeve in the unscrewing direction thereby maintaining the coupling of the inner sleeve to the outer sleeve, and
wherein a tip of the shaft is provided with a cone supported in a bearing cap.

2. The torque limiter as claimed in claim 1, wherein the snap sleeve is fixed to rotate with the outer sleeve by a drive element provided on the inner wall of the outer sleeve, said drive element protruding radially inwardly and engaging in a slot in the snap sleeve.

3. The torque limiter as claimed in claim 1, wherein the rolling elements are pins and the rolling element receiving areas are slots.

4. The torque limiter as claimed in claim 1, wherein the snap sleeve is made of a polyetheretherketone (PEEK).

5. The torque limiter as claimed in claim 1, wherein the torque limiter comprises a receptacle designed to receive a medical instrument, wherein, by means of a plain bearing and a slide sleeve, the receptacle is integrated angular-stable into the torque limiter and is supported almost frictionless in the outer sleeve.

* * * * *